(12) United States Patent
Sommer et al.

(10) Patent No.: US 10,111,732 B2
(45) Date of Patent: *Oct. 30, 2018

(54) SELF-LIGATING BRACKET

(71) Applicant: American Orthodontics Corporation, Sheboygan, WI (US)

(72) Inventors: Jay S. Sommer, Howards Grove, WI (US); Eric W. Nimmer, Plymouth, WI (US); Andrew R. Pietzner, Sheboygan, WI (US)

(73) Assignee: American Orthodontics Corporation, Sheboygan, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/263,511

(22) Filed: Sep. 13, 2016

(65) Prior Publication Data

US 2016/0374781 A1 Dec. 29, 2016

Related U.S. Application Data

(63) Continuation of application No. 14/212,616, filed on Mar. 14, 2014, now Pat. No. 9,468,505.

(60) Provisional application No. 61/787,636, filed on Mar. 15, 2013.

(51) Int. Cl.
*A61C 7/28* (2006.01)
*A61C 7/30* (2006.01)

(52) U.S. Cl.
CPC ............... *A61C 7/287* (2013.01); *A61C 7/30* (2013.01)

(58) Field of Classification Search
CPC .... A61C 7/12; A61C 7/14; A61C 7/28; A61C 7/30; A61C 7/287

USPC ...................................................... 433/8–24
See application file for complete search history.

(56) References Cited

U.S. PATENT DOCUMENTS

| 2,549,528 A | 4/1951 | Russell |
| 2,671,964 A | 3/1954 | Russel et al. |
| 3,131,474 A | 5/1964 | Johnson |
| 4,197,642 A | 4/1980 | Wallshein |

(Continued)

FOREIGN PATENT DOCUMENTS

| DE | 4407100 | 9/1995 |
| DE | 102009029834 A1 | 12/2010 |

(Continued)

OTHER PUBLICATIONS

Agility Self-Ligating Passive System by Orthodontic Design and Production, Inc., acquired Mar. 10, 2014.

(Continued)

*Primary Examiner* — Matthew Nelson
(74) *Attorney, Agent, or Firm* — Andrus Intellectual Property Law, LLP

(57) ABSTRACT

A self-ligating bracket includes a bracket body with a mesial and a distal channel. A spring clip includes a distal arm with a distal arm body and a distal finger and a mesial arm with a mesial arm body and a mesial finger. The spring clip is slidably secured within the bracket body by a sliding engagement of the distal arm with the distal channel and the mesial arm with the mesial channel. The spring clip is movable between an open position and a closed position wherein in the open position, the arch wire slot is unobstructed and in the closed position the mesial finger and distal finger extend into and across the arch wire slot to occlude the arch wire slot.

21 Claims, 8 Drawing Sheets

(56) References Cited

U.S. PATENT DOCUMENTS

| | | |
|---|---|---|
| 4,248,588 A | 2/1981 | Hanson |
| 4,419,078 A | 12/1983 | Pletcher |
| 4,492,573 A | 1/1985 | Hanson |
| 5,094,614 A | 3/1992 | Wildman |
| 5,275,557 A | 1/1994 | Damon |
| 5,322,435 A | 6/1994 | Pletcher |
| 5,429,500 A | 7/1995 | Damon |
| 5,439,378 A | 8/1995 | Damon |
| 5,466,151 A | 11/1995 | Damon |
| 5,474,445 A | 12/1995 | Voudouris |
| 5,474,446 A | 12/1995 | Wildman et al. |
| 5,562,444 A | 10/1996 | Heiser et al. |
| 5,613,850 A | 3/1997 | Wildman et al. |
| 5,630,715 A | 5/1997 | Voudouris |
| 5,711,666 A | 1/1998 | Hanson |
| 5,800,162 A | 9/1998 | Shimodaria et al. |
| 5,857,849 A | 1/1999 | Kurz |
| 5,857,850 A | 1/1999 | Voudouris |
| 5,908,293 A | 6/1999 | Voudouris |
| 5,913,680 A | 6/1999 | Voudouris |
| 6,071,118 A | 6/2000 | Damon |
| 6,071,119 A | 6/2000 | Christoff |
| 6,168,428 B1 | 1/2001 | Voudouris |
| 6,247,923 B1 | 6/2001 | Vashi |
| 6,257,883 B1 | 7/2001 | Voudouris |
| 6,325,622 B1 | 12/2001 | Kelly et al. |
| 6,368,105 B1 | 4/2002 | Voudouris et al. |
| 6,464,495 B1 | 10/2002 | Voudouris |
| 6,554,612 B2 | 4/2003 | Georgakis et al. |
| 6,632,088 B2 | 10/2003 | Voudouris |
| 6,659,766 B2 | 12/2003 | Abels et al. |
| 6,733,286 B2 | 5/2004 | Abels et al. |
| 6,776,613 B2 | 8/2004 | Orikasa |
| 6,843,651 B2 | 1/2005 | Orikasa |
| 6,939,133 B2 | 9/2005 | Voudouris |
| 7,104,791 B2 | 9/2006 | Hanson |
| 7,214,057 B2 | 5/2007 | Voudouris |
| 7,247,019 B2 | 7/2007 | Abels et al. |
| 7,255,557 B2 | 8/2007 | Forster |
| 7,267,545 B2 | 9/2007 | Oda |
| 7,335,020 B2 * | 2/2008 | Castner .................. A61C 7/287 433/11 |
| 7,416,408 B2 | 8/2008 | Farzin-Nia et al. |
| 7,419,375 B2 | 9/2008 | Farzin-Nia et al. |
| 7,442,039 B2 | 10/2008 | Opin |
| 7,481,651 B2 | 1/2009 | Sernetz et al. |
| 7,611,353 B2 * | 11/2009 | Sommer .................. A61C 7/28 433/10 |
| 7,621,743 B2 | 11/2009 | Bathen et al. |
| 7,704,072 B2 | 4/2010 | Damon |
| 7,785,101 B2 | 8/2010 | Forster |
| 7,845,939 B2 | 12/2010 | Minium |
| 7,909,603 B2 | 3/2011 | Oda |
| 7,963,767 B2 | 6/2011 | Lewis et al. |
| 8,029,276 B1 * | 10/2011 | Lokar .................. A61C 7/287 433/10 |
| 8,033,824 B2 | 10/2011 | Oda et al. |
| 8,038,438 B2 * | 10/2011 | Ruiz Diaz .................. A61C 7/14 433/11 |
| 8,113,827 B2 | 2/2012 | Farzin-Nia et al. |
| 8,246,348 B2 * | 8/2012 | Heiser .................. A61C 7/14 433/10 |
| 8,246,349 B2 | 8/2012 | Scommegna et al. |
| 8,251,696 B2 | 8/2012 | Rodriguez et al. |
| 8,282,392 B2 | 10/2012 | Hilliard |
| 8,297,970 B2 * | 10/2012 | Kanomi .................. A61C 7/14 433/11 |
| 8,393,896 B2 | 3/2013 | Oda |
| 8,414,292 B2 | 4/2013 | Lopes |
| 8,568,138 B2 | 10/2013 | Farzin-Nia et al. |
| 8,585,398 B2 | 11/2013 | Yeh et al. |
| 8,636,507 B2 * | 1/2014 | Voudouris .................. A61C 7/14 433/10 |
| 8,726,510 B2 | 5/2014 | Voudouris |
| D710,998 S | 8/2014 | Voudouris |
| 8,906,486 B2 | 12/2014 | Fontaine |
| 8,932,053 B2 | 1/2015 | Curiel et al. |
| 8,944,811 B2 | 2/2015 | Curiel et al. |
| 2002/0187452 A1 | 12/2002 | Abels et al. |
| 2003/0039938 A1 | 2/2003 | Orikasa |
| 2004/0166459 A1 | 8/2004 | Voudouris |
| 2004/0170942 A1 | 9/2004 | Heiser |
| 2004/0175667 A1 | 9/2004 | Abels et al. |
| 2004/0175669 A1 | 9/2004 | Abels et al. |
| 2004/0175699 A1 | 9/2004 | Fizman |
| 2005/0239012 A1 | 10/2005 | Bathen et al. |
| 2005/0244772 A1 | 11/2005 | Abels et al. |
| 2007/0072143 A1 * | 3/2007 | Sommer .................. A61C 7/28 433/10 |
| 2007/0166658 A1 | 7/2007 | Voudouris |
| 2007/0178422 A1 | 8/2007 | Voudouris |
| 2009/0004617 A1 | 1/2009 | Oda et al. |
| 2009/0325119 A1 | 12/2009 | Sierk |
| 2010/0105000 A1 | 4/2010 | Scommegna et al. |
| 2010/0261131 A1 | 10/2010 | Ruiz-Vela et al. |
| 2010/0311004 A1 | 12/2010 | Voudouris |
| 2011/0076633 A1 * | 3/2011 | Bryant .................. A61C 7/287 433/11 |
| 2011/0136071 A1 | 6/2011 | Levens |
| 2012/0028206 A1 * | 2/2012 | Lopes .................. A61C 7/287 433/10 |
| 2013/0125398 A1 | 5/2013 | Curiel et al. |
| 2013/0171579 A1 | 7/2013 | Orikasa et al. |
| 2013/0196279 A1 | 8/2013 | Curiel et al. |
| 2013/0260329 A1 | 10/2013 | Voudouris |
| 2013/0337397 A1 | 12/2013 | Curiel et al. |
| 2013/0337399 A1 | 12/2013 | Curiel et al. |
| 2014/0011154 A1 | 1/2014 | Curiel et al. |
| 2014/0023981 A1 | 1/2014 | Voudouris |
| 2014/0134563 A1 | 5/2014 | Voudouris |
| 2014/0199648 A1 | 7/2014 | Lopes |
| 2014/0212828 A1 | 7/2014 | Falcone et al. |
| 2014/0272750 A1 | 9/2014 | Lai |
| 2014/0272753 A1 | 9/2014 | Sommer et al. |
| 2014/0308622 A1 | 10/2014 | Voudouris |
| 2015/0125804 A1 | 5/2015 | D'Amico Neto |
| 2015/0216629 A1 | 8/2015 | Voudouris |
| 2015/0265377 A1 | 9/2015 | Wu et al. |

FOREIGN PATENT DOCUMENTS

| | | |
|---|---|---|
| EP | 161831 | 3/1996 |
| EP | 1234549 | 8/2002 |
| EP | 1287789 | 3/2003 |
| EP | 2644150 A1 | 10/2013 |
| FR | 2922753 | 12/2010 |
| WO | 1998020805 | 5/1998 |
| WO | 2006094403 | 9/2006 |
| WO | 2008044912 | 4/2008 |
| WO | 2010028276 | 3/2010 |
| WO | 2010103178 | 9/2010 |

OTHER PUBLICATIONS

European Search Report in co-pending Appln No. 14000960.6, dated Aug. 28, 2014.

Easy Clip, Self-Ligating Bracket Systems Brochure by Great Lakes Orthodontics, LTD, Oct. 2015.

* cited by examiner

SELF-LIGATING BRACKET

CROSS-REFERENCE TO RELATED APPLICATIONS

This application is continuation of U.S. application Ser. No. 14/212,616, filed Mar. 14, 2014, which application was published on Sep. 18, 2014, as U.S. Publication No. US20140272753, which application claims priority from U.S. Provisional Application Ser. No. 61/61/221,363 filed on Sep. 21, 2015, all of which are hereby incorporated by reference in their entireties.

BACKGROUND

The present disclosure relates to the field of orthodontics. More specifically, the present disclosure relates to self-ligating brackets.

Orthodontic treatment often includes at least a combination of an arch wire and brackets and/or buccal tubes that are used to secure the arch wire to the teeth of the patient. The arch wire is made of a resilient material that, if bent or deformed, will return to its previous shape. Dental malocclusions are treated by securing the arch wire to the patient's teeth which are brought into a post-treatment alignment as the arch wire returns to its original shape.

Traditionally, brackets are secured to the teeth of a patient and the brackets have an arch wire slot within which the arch wire is received. Elastomeric ligatures secure the arch wire within the arch wire slot of the bracket. Self-ligating brackets eliminate the need for separate elastomeric ligatures by mechanically securing the arch wire to the bracket.

BRIEF DISCLOSURE

An exemplary embodiment of a self-ligating bracket assembly includes a bracket body having a mesial side and a distal side. The bracket body includes an arch wire slot that extends from the mesial side to the distal side of the bracket body. A mesial channel extends into the bracket body from the mesial side. A distal channel extends into the bracket body from the distal side. A spring clip includes a distal arm and a mesial arm. The distal arm includes a distal arm body and a distal finger. The mesial arm body includes a mesial arm and a mesial finger. The distal finger and the mesial finger extend in a plane different from the distal arm body and the mesial arm body. The spring clip is slidably secured within the bracket body by respective sliding engagement of the distal arm with the distal channel and the mesial arm with the mesial channel. The spring clip is moveable between an open position and a closed position wherein in the open position, the arch wire slot is unobstructed and in a closed position, the mesial finger and the distal finger extend into and across the arch wire slot to occlude the arch wire slot.

In an exemplary additional embodiment of a self-ligating bracket assembly, a bracket body includes a mesial side and a distal side. The bracket body further includes an arch wire slot that extends from the mesial side to the distal side of the bracket body. The arch wire slot is at least partially defined by a mesial shoulder and a distal shoulder. The bracket body further includes a mesial channel that extends into the bracket body from the mesial side. The bracket body includes a distal channel that extends into the bracket body from the distal side. A spring clip includes a distal arm and a mesial arm. The distal arm includes a distal arm body that extends in a first plane connected to a distal finger that extends in the second plane by a distal transition portion. The mesial arm includes a mesial arm body that extends in the first plane connected to a mesial finger that extends in the second plane by a mesial transition portion. The spring clip is slidably secured to the bracket body and moveable between an open position and a closed position by respective sliding engagement of the distal arm with the distal channel and the mesial arm with the mesial channel. When the spring clip is in the open position, the arch wire slot is unobstructed. When the spring clip is in the open position, the mesial finger is further slidably received within the mesial channel and deformed within the mesial channel such that the mesial finger is generally co-planar with the mesial arm body and the distal finger is slidably received within the distal channel and deformed within the distal channel such that the distal finger is generally co-planar with the distal arm body. When the spring clip is in the closed position, the mesial finger extends out of the mesial channel and the distal finger extends out of the distal channel into and across the arch wire slot to occlude the arch wire slot. When the spring clip is in the closed position the distal transition portion further resiliently engages the distal shoulder and the mesial transition portion resiliently engages the mesial shoulder. Further, when the spring clip is in the closed position, the mesial finger and the distal finger are configured to apply an active retaining force against an arch wire received within the arch wire slot.

DETAILED DISCLOSURE

Figure 1A:
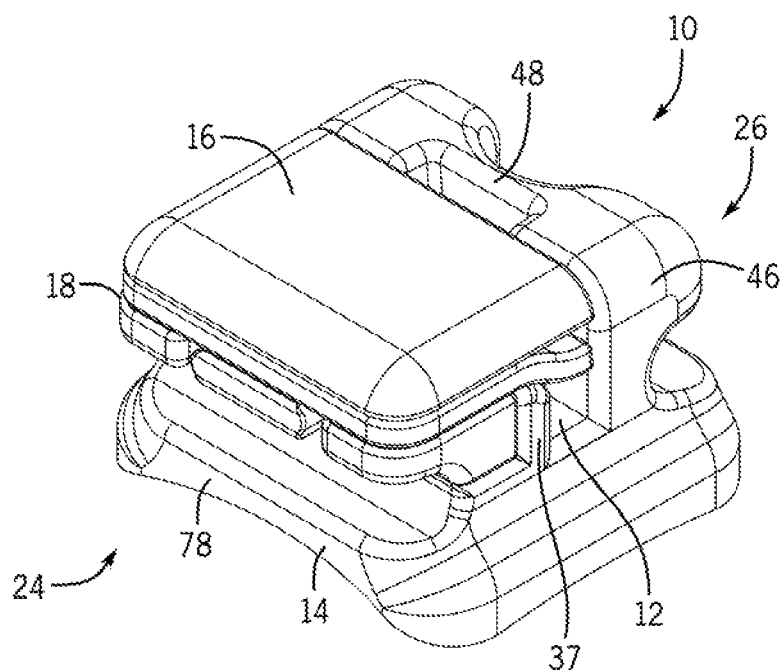
FIG. 1A is a perspective view of an exemplary embodiment of a self-ligating bracket in a closed configuration.
Figure 1B:
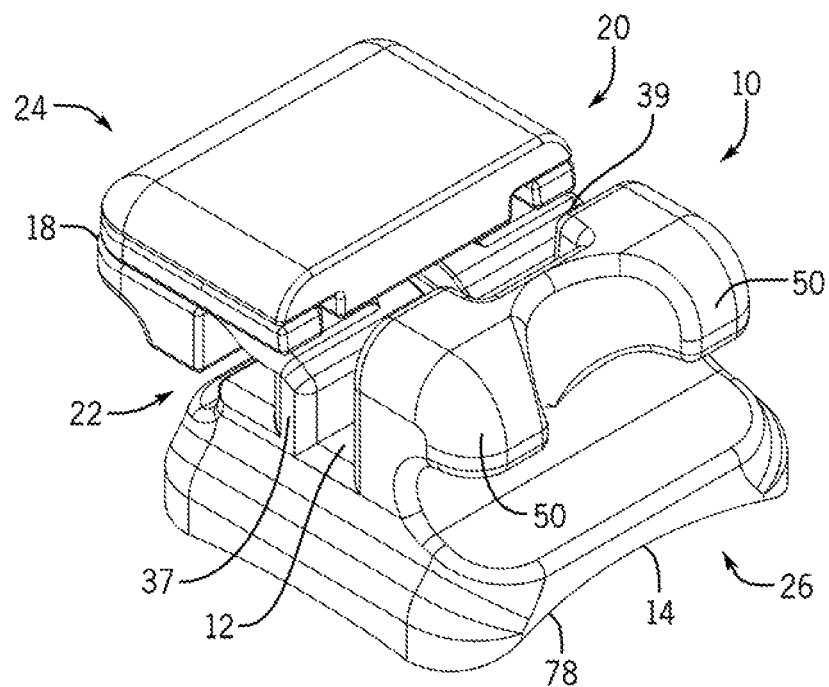
FIG. 1B is a perspective view of an exemplary embodiment of the self-ligating bracket in an open configuration.
Figure 2A:
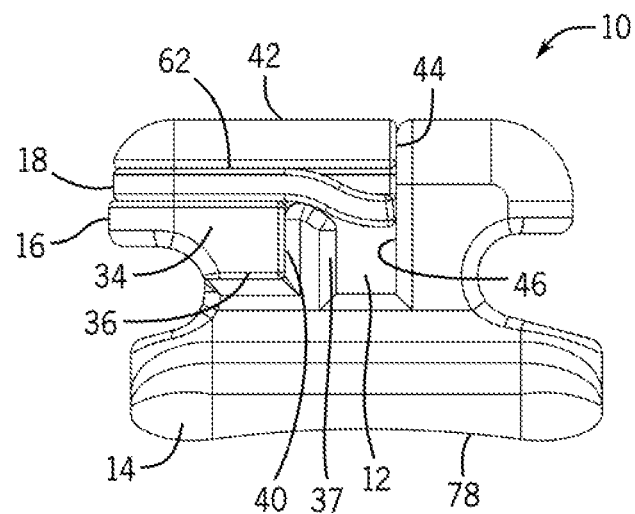
FIG. 2A is a side view of an exemplary embodiment of the self-ligating bracket in the closed configuration.
Figure 2B:
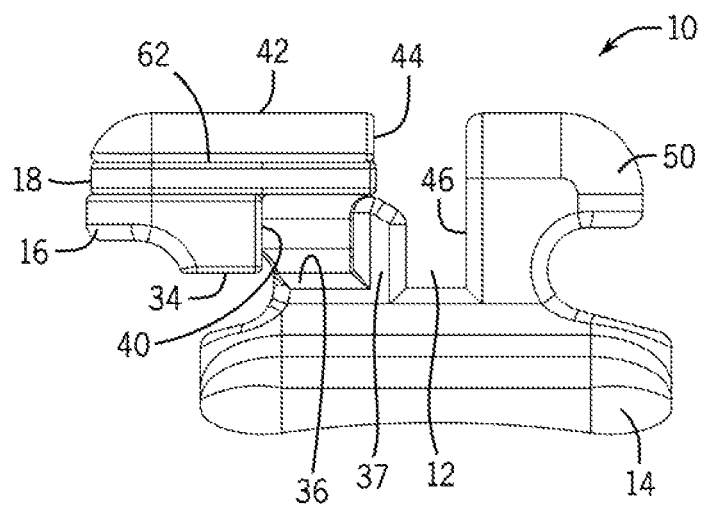
FIG. 2B is a side view of an exemplary embodiment of the self-ligating bracket in the open configuration.
Figure 3:
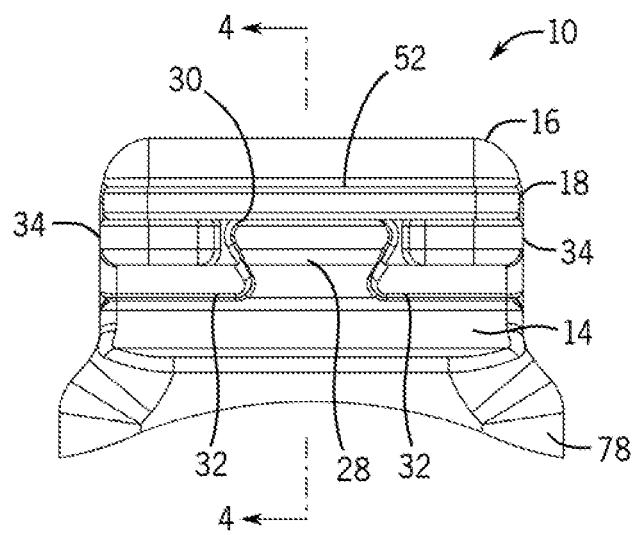
FIG. 3 is an occlusal view of an exemplary embodiment of the self-ligating bracket.
Figure 4:
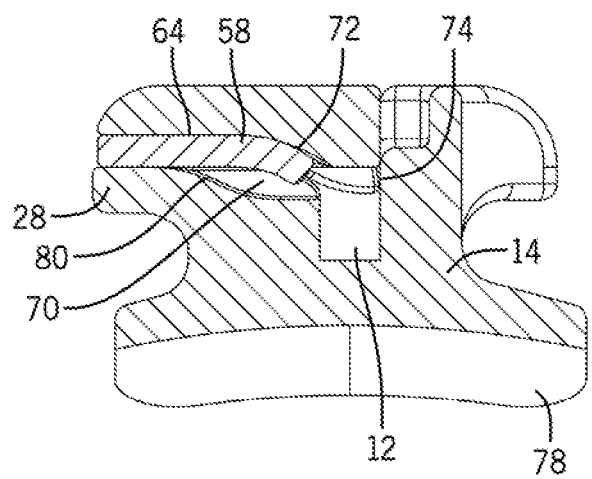
FIG. 4 is a sectional side view of an exemplary embodiment of the self-ligating bracket taken along line 4-4 of FIG. 3.
Figure 5:
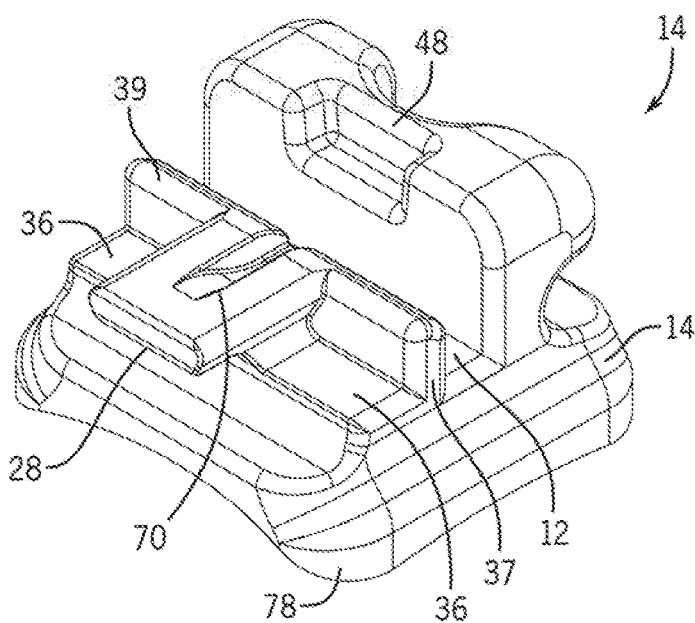
FIG. 5 depicts an exemplary embodiment of a base portion.

FIGS. 1A-4 all depict an exemplary embodiment of a self-ligating bracket 10. FIGS. 1A and 2A depict the self-ligating bracket 10 in a closed configuration while FIGS. 1B and 2B depict the self-ligating bracket 10 in an open configuration. The self-ligating bracket 10 moves between the open configuration wherein an arch wire (not depicted) can be inserted into and received into an arch wire slot 12 of the self-ligating bracket 10 and a closed configuration wherein the arch wire slot 12 is occluded, such as to exemplarily retain an arch wire (not depicted) within the arch wire slot 12.

Figure 6:
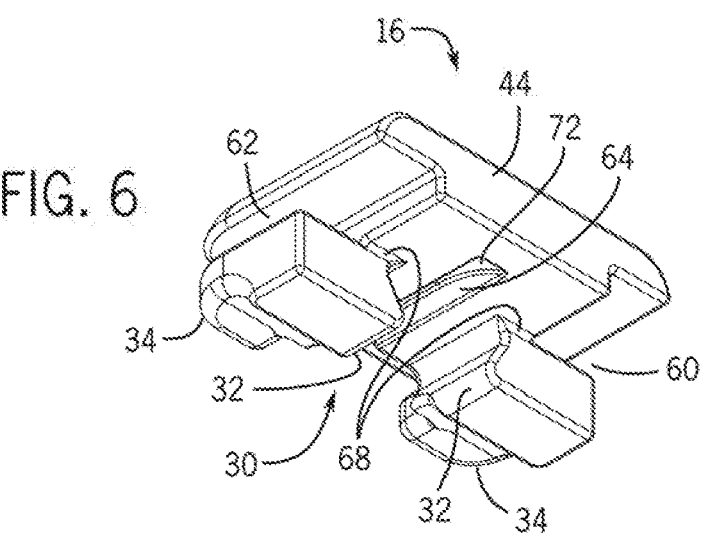
FIG. 6 depicts an exemplary embodiment of a cover portion.
Figure 7:
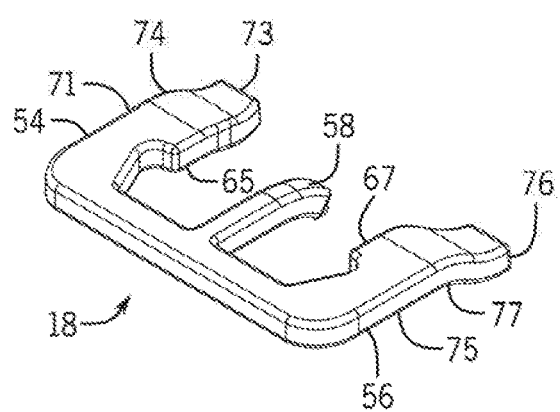
FIG. 7 depicts an exemplary embodiment of a spring clip.

The self-ligating bracket 10 includes a bracket body 13 that includes a base portion 14 and a cover portion 16. The self-ligating bracket 10 further includes a spring clip 18. The base portion 14 is depicted in greater detail in FIG. 6. The cover portion 16 is depicted in greater detail in FIG. 7. While the base portion 14 and cover portion 16 are depicted as separate structure, as will be described in additional embodiments herein, the bracket body 13, including the base portion 14 and cover portion 16, may also be a unitary construction. The spring clip 18 is depicted in greater detail in FIG. 7. In exemplary embodiments as described herein, the spring clip 18 is moveable between an open position wherein the self-ligating bracket 10 is in the open configuration and a closed position wherein the self-ligating bracket 10 is in the closed configuration. The self-ligating bracket 10 includes a distal side 20 and a mesial side 22, an occlusal side 24, and gingival side 26. It is recognized that the identifications of the distal side 20, mesial side 22, occlusal side 24, and gingival side 26 are merely exemplary of relative designations and it is recognized that in alternative embodiments, self-ligating brackets may be oriented within the patient's mouth in an alternative arrangement, resulting in differing relative orientations. Therefore, it is understood that the relative and orientational references as used herein are merely exemplary and used in a relative sense such that the present disclosure would similarly apply to embodiments of self-ligating brackets configured for alternative orientations within the patient's mouth.

The exemplary embodiment of the self-ligating bracket 10 is described herein with general reference to FIGS. 1-7, and reference to specific figures when noted. As disclosed above, the bracket body 13 exemplarily includes the base portion 14 and the cover portion 16. The cover portion 16 is slidably secured to the base portion 14 by engagement of a lip 28 of the base portion 14 with a slot 30 in the cover portion 16. In an embodiment, the lip 28 is configured as a dovetail and the slot 30 is configured as a dovetail slot with opposed projections 32 configured to engage the dovetail of the lip 28 (see FIG. 3). The projections 32 are extensions of arm 34 that form a lingual-most portion of the cover portion 16. The cover portion 16 slides or otherwise translates along the lip 28 of the base portion 14 due to engagement of the lip 28 by the slot 30. The arms 34 of the cover portion 16 engage and translate along ledges 36 of the base portion 14. The base portion 14 further includes mesial shoulder 37 and distal shoulder 39 which on the gingival side define the occlusal side of arch wire slot 12 through the base portion 14 and the gingival sides of the mesial shoulder 37 and distal shoulder 39 create a stop at which occlusal sides 40 of the arms 34 engage, when the self-ligating bracket 10 is in a closed configuration. As described above, the mesial shoulder 37 and distal shoulder 39 define the occlusal side of the arch wire slot 12. The opposite or gingival side of the arch wire slot 12 is defined by a tie wing face 46. The base portion 14 terminates at the gingival end with a pair of tie wings 50. The cover portion 16 further includes a front face 42. In an exemplary embodiment, the front face 42 may be the labial face 42 as when the bracket 10 is secured to a patient's tooth the face 42 is directed outward from the tooth in the labial direction.

Comparing the open configuration and closed configuration of the self-ligating bracket 10, when the self-ligating bracket 10 is in an open configuration, the cover portion 16 is translated along the lip 28 of the base portion 14 such as to expose the arch wire slot 12 in order to receive an arch wire (not depicted) inserted into the arch wire slot 12. When the self-ligating bracket 10 is in a closed configuration, a surface 44 of the cover portion 16 engages the tie wing face 46 of the base portion 14 that defines a side of the arch wire slot 12. The base portion 14 includes a detent 48 between the opposed tie wings 50. As described in further detail herein, an orthodontist can insert a tool into the detent 48 in order to create a force between the base portion 14 at the detent 48 and the surface 44 of the cover portion 16 in order to move the self-ligating bracket from the closed configuration to the open configuration.

The self-ligating bracket 10 further includes a spring clip 18 as mentioned above and specifically depicted in FIG. 7. The spring clip 18 is inserted into a spring clip channel 52 of the cover portion 16. The spring clip channel 52 extends into a distal channel 60, a mesial channel 62, and a central channel 64.

The spring clip 18 includes a distal arm 54 and a mesial arm 56 as opposed side arms, as well as a center arm 58. The distal arm 54 exemplarily includes a distal arm body 71, a distal finger 73, and a distal transition portion 74. The mesial arm 56 exemplarily includes a mesial arm body 75, a mesial finger 76, and a mesial transition portion 77. The spring clip 18 is inserted into the spring clip channel 52 of the cover portion 16 and the respective distal arm 54, mesial arm 56, and center arm 58 are inserted into the respective distal channel 60, mesial channel 62, and central channel 64. The distal arm 54 and the mesial arm 56 respectively include a distal projection 65 and a mesial projection 67 that securingly engage the respective arms 34 of the cover portion 16. As the clip 18 is inserted into the spring clip channel 52, the distal arm 54 and the mesial arm 56 resiliently deform outwards in order to move the projections 65, 67 past the arms 34, until the spring clip 18 is fully in position in the spring clip channel 52 at which point the projection 65, 67 move past the arms 34 and engage an engagement faces 68 of the arms 34. The engagement of the projections 65, 67 with the engagement faces 68 of the arms 34 secures the spring clip 18 to the cover portion 16. In such an embodiment, the engagement faces 68 and the arms 34 act as stop projections to resiliently secure the spring clip 18 to the cover portion 16 of the bracket body 11.

The center arm 58 is positioned within the central channel 64 of the cover portion 16 and a central channel 70 of the base portion 14. The central channel 64 of the cover portion 16 includes a curved surface 72 that lingually deforms the center arm 58 into the central channel 70 of the base portion 14. This deformation of the center arm 58 of the spring clip 18 places an upwardly directed biasing force on the cover, which helps to secure the cover to the base portion 14 to form the bracket body 11 by interaction of the dovetailed lip 28 of the base portion 14 and slot 30 of the cover portion 16.

The spring clip 18 further includes a distal finger 73 at the end of the distal arm 52 and a mesial finger 76 at the end of the mesial arm 56. The fingers 73, 76 are configured at a lower plane than that of the rest of the spring clip 18, particularly the distal arm body 71 and the mesial arm body 75. This is exemplarily achieved by distal transition portion 74 and mesial transition portion 77, which may exemplarily by S-curves, but will be recognized to be able to be configured in alternative shapes or angles and achieve transition between the respective arm bodies 71, 75 and the fingers 73, 76. When the bracket 10 is in the closed configuration, the fingers 73, 76 extend past the shoulders 37, 39 of the base portion 14 and into the arch wire slot 12. In order to move the spring clip 18 into the open position, the fingers 73, 76 at the transition portions 74, 77 must be deformed such as to move past the shoulders 37, 39 of the base portion 14. This creates a resilient force that when the bracket 10 is in the closed configuration, biases the spring clip 18 to stay in the closed position. This also creates a positive closure, such that the cover portion 16 is only closed if the fingers 73, 76 have moved past the shoulders 37, 39 into the arch wire slot 12.

In use, a plurality of self-ligating brackets 10 are secured to the teeth forming a dentition of a patient. In embodiments, the self-ligating bracket 10 includes a bonding pad 78 to which an adhesive or other bonding material is applied. The bonding pad 78 forms the interface between the self-ligating bracket 10 and the patient's tooth. It is to be recognized that in some embodiments, the bonding pad 78 may be an integral component with the self-ligating bracket, while in other embodiments, the self-ligating bracket base is welded or brazed to a separate pad.

Once the self-ligating brackets 10 are placed on the teeth of the patient, the orthodontist begins the process of inserting the arch wire into the arch wire slots 12. If the spring clips 18 of the self-ligating brackets 10 are not open, the orthodontist opens the spring clips 18 by inserting a dental tool into the detent 48 and applying a force between the detent 48 and the top surface 44 of the cover portion 16. In some embodiments, this exemplarily may be performed using a scaler. A sufficient force is required in order to overcome the resiliency of the spring clip 18 to flatten at least the transition portions 74, 77 in order to move the fingers 73, 76 past the shoulders 37, 39 of the base portion 14. Once these mechanical features are overcome, the cover portion 16 and the spring clip 18 slides or translates along the interface of the slot 30 of the cover portion 16 and the lip 28 of the base portion 14 to move the self-ligating bracket 10 into the open configuration. A bottom end 80 of the central channel 70 defines the lowermost extent to which the cover portion 16 and spring clip 18 can be translated with respect to the base portion 14. The center arm 58, lingually deformed by the curved surface 72 of the central channel 64 of the cover portion 16 and spring clip 18, engages the bottom end 80 of the central channel 70 of the base portion 14, which prevents further translation of the cover portion 16 and spring clip 18 along the lip 28.

Once in the open configuration, the arch wire (not depicted) can be inserted into the arch wire slot 12 and a compressive force is applied between the cover portion 16 and spring clip 18 and the gingival side 26 of the base portion 14 (exemplarily the tie wings 50) in order to reverse the opening process and move the cover portion 16 and spring clip 18 into the closed position. In an exemplary embodiment, while the process to move the self-ligating bracket 10 into the open configuration requires the use of a dental tool, the self-ligating bracket 10 may be moved into the closed configuration with forces exemplarily applied by the finger and thumb of the orthodontist.

The orthodontist can confirm or is assured that the self-ligating bracket is fully in the closed configuration as the mechanical interactions of the spring clip 18 and cover portion 16 with the base portion 14 provides a positive closure that may be heard and/or felt by the orthodontist. Namely, the fingers 73, 76 must be moved over the shoulders 37, 39, at which point the fingers 73, 76 will return to their original position at a lower plane than the rest of the spring clip 18, and will extend into and across the arch wire slot 12. Further, when the bracket 10 is in the closed configuration, the occlusal sides 40 of the arms 34 also engage the shoulders 37, 39. Thus, in embodiments, when the cover portion 16 and spring clip 18 are in the closed position, the fingers 73, 76 place an active retaining force against the arch wire while the cover portion 16 provides a passive restraint to the arch wire.

When the self-ligating bracket 10 is in the closed configuration, the cover portion 16 provides a mechanical block to the arch wire exiting the arch wire slot 12. Furthermore, the fingers 73, 76 place a resilient force on the arch wire further maintaining the arch wire fully within the arch wire slot 12. The location of the distal arm 54 on the far distal side 20 of the self-ligating bracket 10 and the mesial arm 56 on the far mesial side 22 of the self-ligating bracket 10 place these additional spring forces from the fingers 73, 76 on the arch wire at the respective distal side 20 edge and the mesial side 22 edge to help to further ensure that the arch wire is in contact and fully seated in the arch wire slot 12 at the edges of the bracket 10.

In embodiments, the cover portion 16 and the base portion 14 are assembled together into the bracket base 11 by use of a sliding dovetail joint (e.g. lip 28 and slot 30). After the cover portion 16 is in the fully closed position relative to the base portion 14, a spring clip 18 is assembled into the cover portion 16 which includes the distal channel 60 configured to receive the distal arm 54 of the spring clip 18 and the mesial channel 62 configured to accept the mesial arms 56 of the spring clip 18. A center arm 58 on the spring clip 18 is designed to prevent the cover portion 16 from being pulled off of the base portion 14, in an occlusal direction or a gingival direction, after the bracket 10 has been assembled. The distal arm 54 and the mesial arm 56 of the spring clip 18 are constrained within the respective channels which only permit specific flexures of portions of the spring clip 18. These flexures include the curvature of the center arm 58 into the central channel 70 of the base portion 14 which movably secures the cover portion 16 to the base portion 14. The fingers 73, 76 of the spring clip 18 are permitted to flex to move past the shoulders 37, 39 of the base portion 14 and into the arch wire slot 12 to place an active resilient force on an arch wire at the distal side 20 and mesial side 22 of the bracket 10. The distal arm 54 and mesial arm 56 are permitted to outwardly flex such that the projections 66 of the distal arm 54 and mesial arm 56 can engage and disengage the engagement face 68 of the arm 34 to secure the spring clip 18 to the cover portion 16.

In an embodiment, the spring clip 18 is constructed of a nickel titanium material, which offers superior resistance to permanent deformation forces and can be used to create a spring clip that can endure the deformation forces for the full duration of orthodontic treatment. Furthermore, in embodiments, the nickel titanium material can be heat treated to specific force levels during manufacturing in order to further control the forces placed on the arch wire at the edges of the bracket.

In still further embodiments as depicted herein, the bracket includes large radius corners and edges along with flat facial surfaces. These flatter and smoother surfaces can increase comfort for the patient and can facilitate ease of cleaning and reduce traps for food and/or bacteria in mouth of the patient.

FIGS. 8A-12 all depict an exemplary additional embodiment of a self-ligating bracket 100. The self-ligating bracket 100 generally includes a bracket body 102 and a spring clip 104. In embodiments, a bonding pad 106 is secured to the bracket body 102. The bonding pad 106 may be exemplarily secured to the bracket body 102 by brazing or welding. In alternative embodiments, the bonding pad 106 may be secured to the bracket body 102 by being integral to one another and being exemplarily formed by casting or milling, although it will be understood that alternative techniques of manufacturing the bracket body 102 and bonding pad 106 may be used. In embodiments, the bonding pad 106 may be formed or contoured such as to be secured to a tooth of a patient's dentition.

As described above, the self-ligating bracket 100 exemplarily includes a distal side 108, a mesial side 110, a gingival side 112, and an occlusal side 114. It will be recognized that these designations are relative and informational and alternative embodiments may be positioned in other orientations within the mouth of the patient while remaining within the scope of the embodiments as disclosed herein.

Figure 8A:
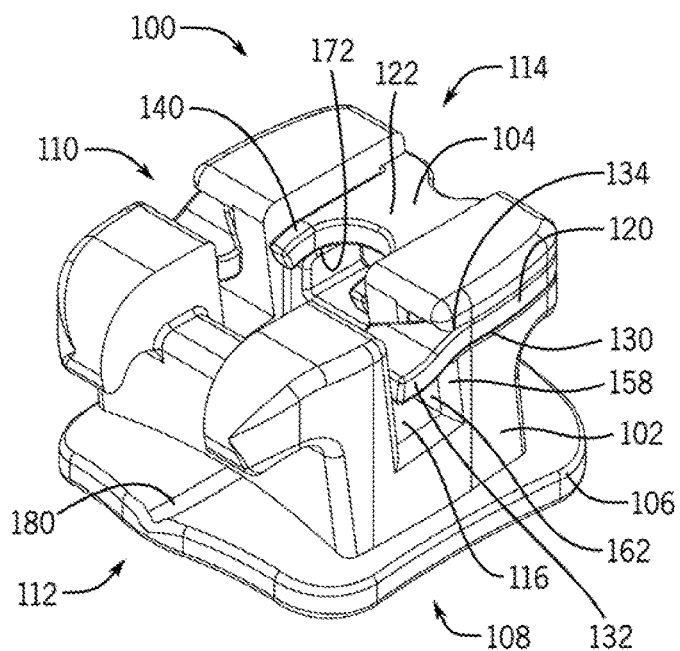
FIG. 8A is a perspective view of an exemplary additional embodiment of a self-ligating bracket in a closed position.
Figure 8B:
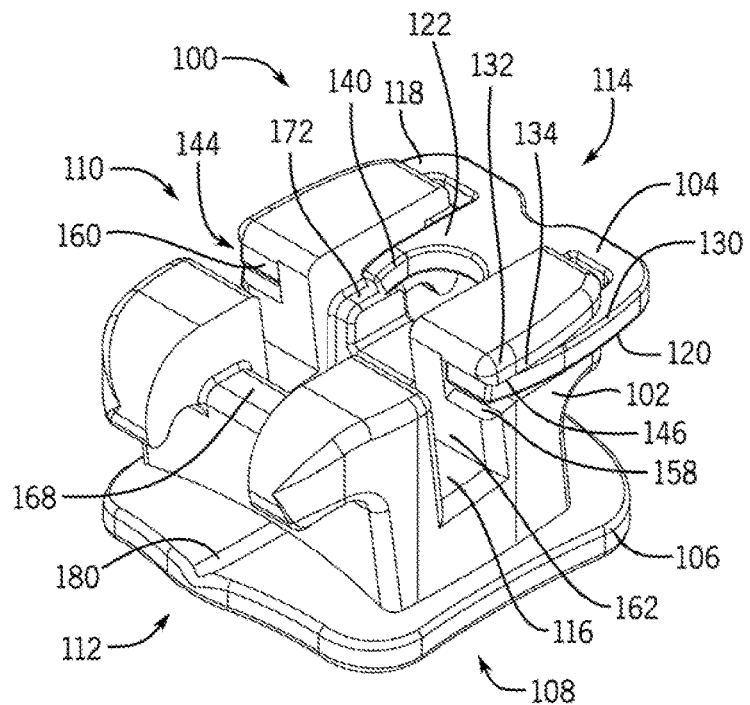
FIG. 8B is a perspective view of the exemplary additional embodiment of the self-ligating bracket in an open position.

FIGS. 8A and 8B are perspective views of the embodiment of the self-ligating bracket 100 that alternatingly depict the self-ligating bracket 100 with the spring clip 104 moved between the closed position (FIG. 8A) and the spring clip 104 in the open position (FIG. 8B). The bracket body 102 includes an arch wire slot 116 that is configured to receive an arch wire (e.g. arch wire 178 FIG. 12) when the self-ligating bracket 100 is used in orthodontically treating the dentition of a patient. When the spring clip 104 is in the open position (FIG. 8B), the arch wire slot 116 is able to receive an arch wire. When the spring clip 104 is in the closed position (FIG. 8A), the spring clip 104 operates to retain the arch wire (e.g. FIG. 12) within the arch wire slot 116, as will be described in further detail herein.

Figure 9:
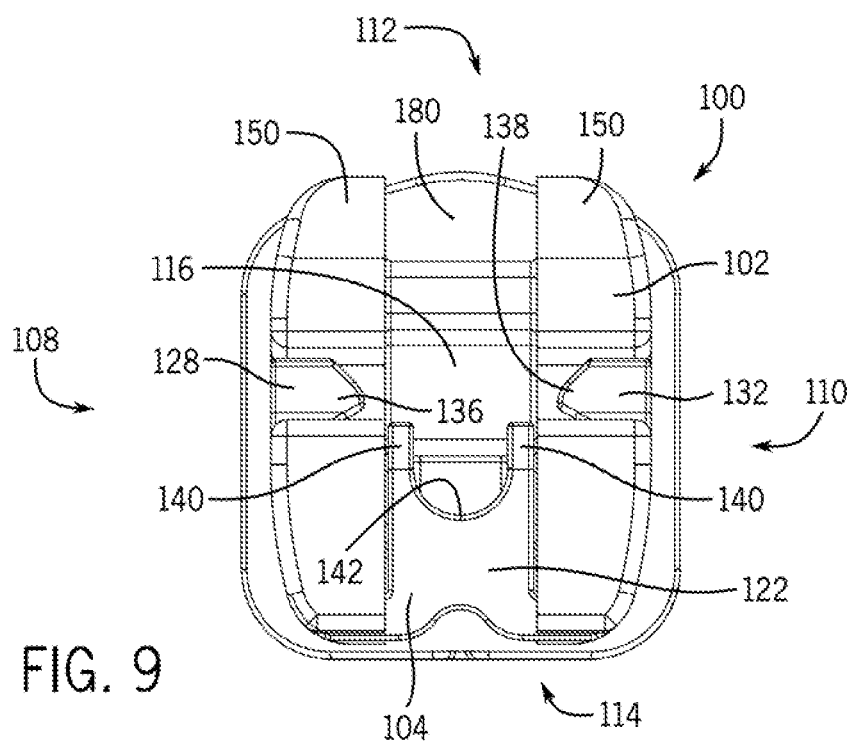
FIG. 9 is a top view of the exemplary additional embodiment of the self-ligating bracket.
Figure 10:
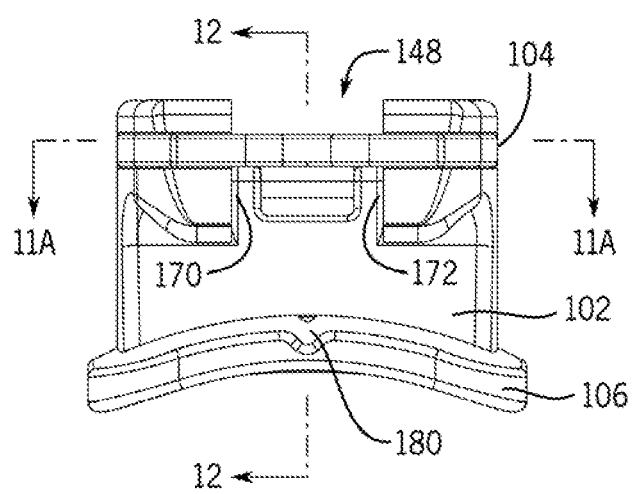
FIG. 10 is a side view of the exemplary additional embodiment of the self-ligating bracket from the occlusal direction.
Figure 11A:
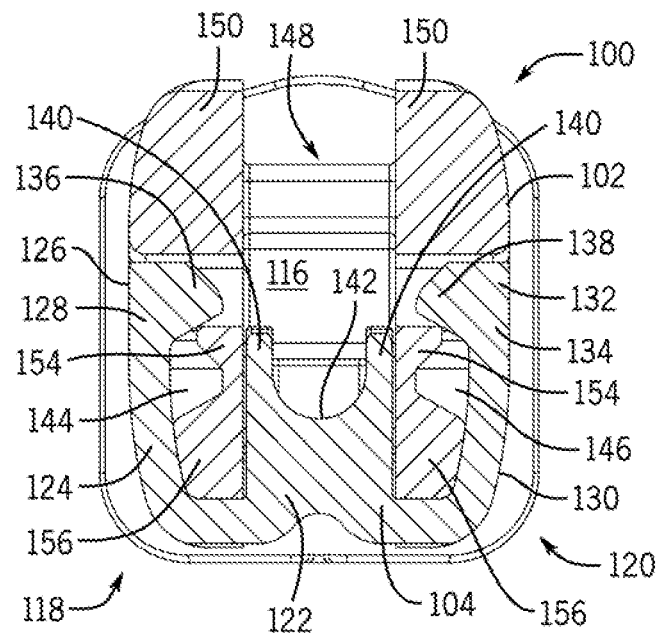
FIG. 11A is a cut away view of the exemplary additional embodiment of the self-ligating bracket taken along line 11-11 of FIG. 10 in the closed position.
Figure 11B:
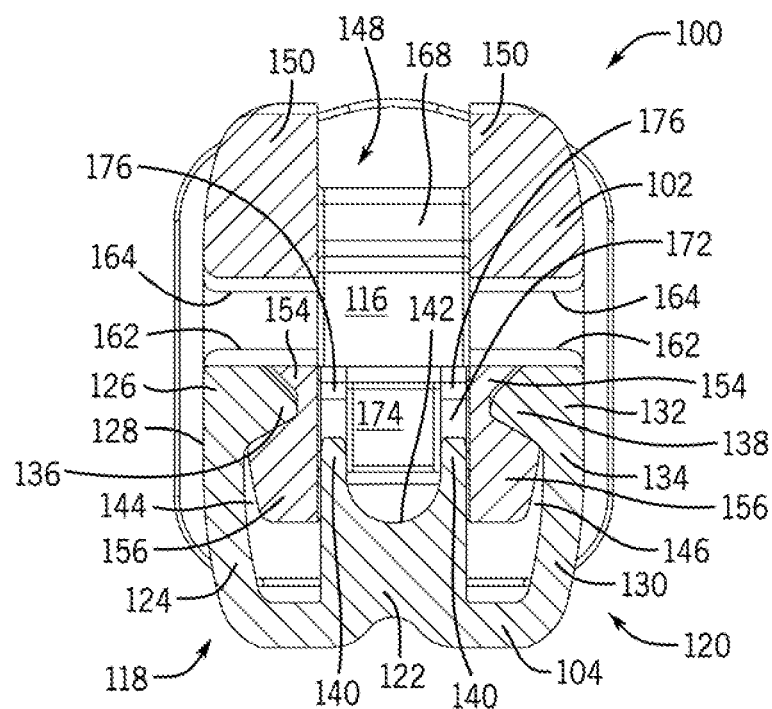
FIG. 11B is a cut away view of the exemplary additional embodiment of the self-ligating bracket taken along line 11-11 of FIG. 10 in the open position.
Figure 12:
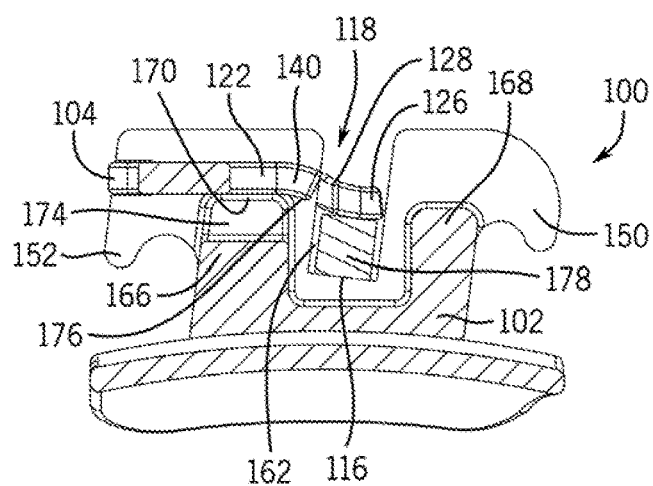
FIG. 12 is a cut away view of the exemplary additional embodiment of the self-ligating bracket taken along line 12-12 of FIG. 10.
Figure 13:
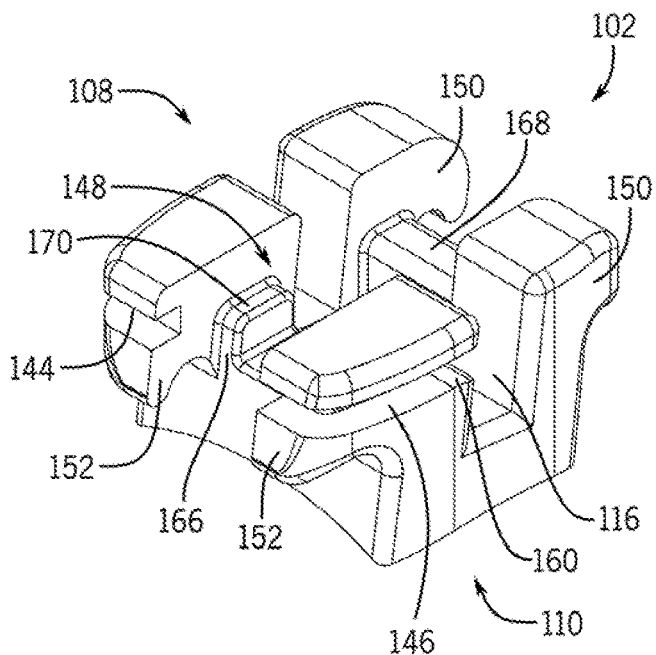
FIG. 13 is a perspective view of an exemplary additional embodiment of a bracket body.
Figure 14:
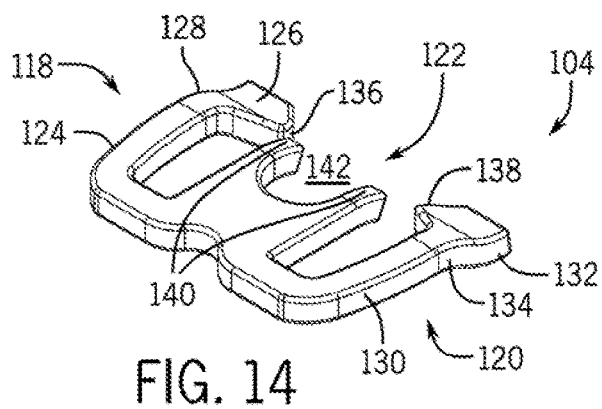
FIG. 14 is a perspective view of an exemplary additional embodiment of a spring clip.

FIG. 9 is a top view of the self-ligating bracket 100 with the spring clip 104 in the closed position. FIG. 10 is a side view of the self-ligating bracket 100 from the gingival side. FIGS. 11A and 11B are cross sectional views of the self-ligating bracket 100 with the spring clip 104 taken along line 11-11 in FIG. 10, respectively in the closed position (FIG. 11A) and the open position (FIG. 11B). FIG. 12 is a cut away view of the self-ligating bracket 100 taken along line 12-12 of FIG. 10. FIG. 13 is a perspective view of an exemplary embodiment of a bracket body 102. FIG. 14 is a perspective view of an exemplary embodiment of a spring clip 104.

The spring clip 104 includes a distal arm 118, a mesial arm 120, and a center arm 122. The distal arm 118 further includes a distal arm body 124 and a distal finger 126. The distal finger 126 is connected to the distal arm body 124 by a distal transition portion 128. In an exemplary embodiment, the distal transition portion 128 is formed as an S-curve between the distal arm body 124 and the distal finger 126 although it will be recognized that the distal transition portion 128 may take a variety of other shapes or forms while staying in the scope of the present disclosure. In embodiments, the distal finger 126 extends in a different plane than the distal arm body 124. In some embodiments, the distal finger 126 may extend parallel to the distal arm body 124, although in other embodiments the distal finger 126 may extend at another angle or curvature.

The mesial arm 120 similarly includes a mesial arm body 130 connected to a mesial finger 132 by a mesial transition portion 134. In embodiments, the mesial arm 120 is constructed in similar manners as described above with respect to the distal arm 118, and within an exemplarily embodiment, the mesial arm 120 may be constructed in a similar manner and form as to the distal arm 118.

In still further embodiments as described herein, the distal arm 118 further includes a distal projection 136. In an embodiments, the distal projection 136 extends interior to the self-ligating bracket 100 from the distal finger 126. Similarly, the mesial arm 120 includes a mesial projection 138 that extends into the self-ligating bracket 100, exemplarily from the mesial finger 132.

In embodiments as described in further detail herein, the center arm 122 further includes a curved tip 140. In the embodiment as depicted in FIGS. 8A-14, the center arm 122 further includes a cut out 142 configured to receive a tool as described in further detail herein. In such an exemplary embodiment, the center arm 122 may exemplarily terminate in two curved tips 140 with the cut out 142 defined between the opposed curved tips 140.

The bracket body 102 includes a distal channel 144 extending interior into the bracket body 102 from the distal side 108 and a mesial channel 146 that extends into the bracket body 102 for from the mesial side 110. The bracket body 102 further includes a central channel 148 that runs down the center of the bracket body 102 in the gingival-occlusal direction. In an embodiment, the central channel is generally transverse to the arch wire slot 116. In embodiments, the central channel 148 separates gingival tie wings 150 and occlusal tie wings 152.

The bracket body 102 further includes a plurality of stop projections, exemplarily gingival stop projections 154 and occlusal stop projections 156 that respectively extend into the distal channel 144 and the mesial channel 146. The stop projections 154, 156 resiliently engage the distal projection 136 and the mesial projection 138, in particular, to define the open position of the spring clip 104. In an embodiment, when the spring clip 104 is in the open position, the distal projection 136 of the spring clip 104 is resiliently engaged between the respective distal gingival stop projection 154 and distal occlusal stop projection 156 and the mesial projection 138 of the spring clip 104 is resiliently engaged between the mesial gingival stop projection 154 and the mesial occlusal stop projection 156. The occlusal stop projections 156 resiliently prevent further translation of the spring clip 104 in the occlusal direction while the gingival stop projections 154 resiliently retain the spring clip 104 in the open position such that an external force, exemplarily provided by the orthodontist, is required in order to move the spring clip 104 from the open position into the closed position.

In embodiments, the gingival stop projections 154 help to create the active closure of the self-ligating bracket 100 in that a resilient force must be overcome in order to move the spring clip 104 from the open position into the closed position, and once moved past a particular point towards the closed position, resilient and/or mechanical forces force the spring clip 104 into the closed position, such as to create a positive closure ensuring that the spring clip 104 has been moved into the closed position. Exemplarily, as a force is applied against the spring clip 104 to move the spring clip 104 from the open position to the closed position sufficient force must be placed against the spring clip 104 in order to outwardly deflect the distal projection 136 and mesial projection 138 past the gingival stop projections 154 in order to move the distal finger 126 and mesial finger 132 into the arch wire slot 116. In embodiments, the distal and mesial projections 136, 138 of the spring clip 104 are angularly shaped on an occlusal side of the distal and mesial projections 136, 138 such that once a peak of the projections moves past the gingival stop projections 154 the spring clip 104 is forced into the closed position. Similarly, in addition to other features as will be described in further detail herein, once the spring clip 104 is in the closed position, a similar force must be placed on the spring clip 104 in order to outwardly deflect the distal projection 136 and mesial projection 138 around the occlusal stop projection 154. This required outward deflection helps to maintain the position of the spring clip 104 in the closed position wherein distal finger 126 and mesial finger 132 extend into and across the arch wire slot 116 as described in further detail herein Similar to that as described above, an angular shape of the distal and mesial projections 136, 138 of the spring clip 104 initially add to a resistance against moving the spring clip 104 out of the closed position, until peaks of the projections (136, 138) pass the gingival stop projections 154, at which point the angular shape of the gingival side of the distal and mesial projections 136, 138 of the spring clip 104 force the spring clip 104 into the open position. This can achieve the added benefit of providing additional force to break up any calculus that has formed on the bracket body 102 and/or spring clip 104 which could inhibit movement of the spring clip 104 between the closed and open positions.

The bracket body 102 further includes a distal shoulder 158 and a mesial shoulder 160 that at least partially define the arch wire slot 116 and exemplarily at least partially define an occlusal side 162 of the arch wire slot 116. As best depicted in FIGS. 8A and 8B the distal finger 126 and the distal transition portion 128 interact with the distal shoulder 158 and the mesial finger 132 and the mesial transition portion 134 interact with the mesial shoulder 160 to further facilitate the positive closure of the self-ligating bracket by retaining the spring clip 104 in the closed position. For the sake of conciseness, the following description with specific reference to the mesial arm 120 of the spring clip 104 and the mesial shoulder 160 of the bracket body 102; however, it will be recognized that this description will similarly apply to the distal arm 118 of the spring clip 104 and the distal shoulder 158 of the bracket body 102.

As best depicted in FIG. 8B, when the spring clip 104 is in the open position, the mesial arm 120 is withdrawn into the mesial channel 146. The mesial channel 146 is dimensioned such that when the mesial arm 120 is withdrawn into the mesial channel 146, the mesial arm 120 is deformed, such that the mesial finger 132 is generally coplanar with the mesial arm body 130. In an embodiment, the deformation of the mesial arm 120 is primarily a deformation or flattening of the mesial transition portion 134. When the spring clip 104 is in the open position, the mesial transition portion 134 is also generally coplanar with the mesial arm body 130. As will be recognized from the description above, when the spring clip 104 is in the open position, the mesial projection 138 is retained between the mesial gingival stop projection 154 and occlusal stop projection 156. Upon movement of the spring clip 104 from the open position depicted at FIG. 8B to the closed position as depicted in FIG. 8A, the mesial finger 132 exits the mesial channel 146 and the mesial finger 132 returns to its original configuration or state wherein the mesial finger 132 is at a plane different from the mesial arm body 130. Exemplarily, the mesial finger 132 as facilitated by the mesial transition portion 134 extends into and across the arch wire slot 116. In an embodiment, the mesial finger 132 engages the gingival side 164 of the arch wire slot 116, exemplarily opposite the occlusal side 162 as at least partially defined by the mesial shoulder 160.

Similar to that as described above with respect to the mesial projections 138 of the spring clip 104, the shape of the mesial transition portion 134 facilitates the positive closure of the spring clip 104. The deformation of the mesial transition portion 134 to move the spring clip 104 into the open position stores potential energy in the spring clip 104. As the spring clip 104 is moved towards the closed position, once the mesial finger 132 exits the mesial channel 146, the potential energy stored in the mesial transition portion 134 is released as the mesial transition portion 134 returns to its normal shape or configuration, this further forces the mesial finger 132 into and across the arch wire slot 116 and the spring clip 104 into the closed position.

When the spring clip 104 is in the closed position, the spring clip 104 is further resiliently restrained within the arch wire slot 116 by engagement of the mesial transition portion 134 with the mesial shoulder 160. Therefore, in embodiments, the resilient engagement between the mesial transition portion 134 and the mesial shoulder 160 adds to the positive closure of the spring clip 104 as once the mesial finger 132 moves past a particular point of the mesial shoulder 160, the engagement of the mesial transition portion 134 and the mesial shoulder 160 will force the spring clip 104 into the closed position. Similarly, this resilient force must be overcome in order to deform the spring clip 104 about the mesial transition portion 134 and the mesial finger 132 at the mesial shoulder 160 in order to make the mesial transition portion 134 and the mesial finger 132 generally coplanar with the mesial arm body 130 such that the mesial arm 120 can be retained in the mesial channel 146 when the spring clip 104 is in the open position.

In an embodiment of the self-ligating bracket 100, within the central channel 148, an occlusal ridge 166 and a gingival ridge 168 further define the arch wire slot 116. As is best depicted in FIGS. 11A-12, a dimension in the gingival-occlusal direction between the occlusal ridge 166 and the gingival ridge 168 is generally greater than a similar dimension of the arch wire slot 116. In exemplarily embodiments, the arch wire slot 116 is angled with respect to the bracket body 102 such as to configure the self-ligating bracket 100 to place torque or rotative forces on an associated tooth as required by an orthodontic prescription. As a non-limiting example, the arch wire slot 116 is exemplarily depicted with a −7° torque, although other torque, although other torque or angulation of the arch wire slot may be used. The additional distance between the occlusal ridge 166 and the gingival ridge 168 facilitates these various torques and angulations of the arch wire slot 116 by creating a bracket body 102 with increased standardized components and dimensions across differences in arch wire slot size, shape, angulation, or torque.

As best seen with reference to FIGS. 11A-12, embodiments of the occlusal ridge 166 may further be constructed to include a distal ledge 170 and mesial ledge 172 separated by a tool cut out 174. In embodiments, the tool cut out 174 of the bracket body 102 aligns with the cut out 142 in the center arm 122 of the spring clip 104, such as to receive the tip of a tool of an orthodontist to facilitate the application a force on the spring clip 104 by the orthodontist such as to move the spring clip 104 from the closed portion into the open position as described herein.

The occlusal ridge 166 further includes a shoulder 176. It is to be recognized, that in embodiments wherein a tool cut out 174 divides the gingival ridge 166 into a distal ledge 170 and a mesial ledge 172, that the shoulder 176 may exemplarily be provided by the distal ledge 170 and the mesial ledge 172. In embodiments, when the spring clip 104 is in the closed position, the curved tip 140 of the center arm 122 resiliently engages the shoulder 176 such as to further place a resistive force to maintain the spring clip 104 in the closed position. As described above with respect to the distal finger 126 and the mesial finger 132, this resistive force must be overcome in order to move the spring clip 104 from the closed position into the open position. The curved tips 140 also promote the positive closure of the spring clip 104 as described herein. Furthermore, when the spring clip 104 is in the open position, the curved tips 140 of the center arm 122 resiliently engage the respective distal ledge 170 and mesial ledge 172. This resilient engagement of the curved tips 140 with the distal ledge 170 and mesial ledge 172 places additional forces on the spring clip 104 such as the keep the spring clip 104 rigid and resist twisting across the spring clip 104, particularly when the spring clip 104 is in the open position or is being moved between the open position and the closed position.

FIG. 12 further exemplarily depicts a cross-sectional view of arch wire 178 disposed within the arch wire slot 116. As previously described above, and as depicted in FIG. 12, the distal finger 126 and the distal transition portion 128 of the distal arm 118 extend into and across the arch wire slot 116 and in embodiments, the distal finger 126 resiliently engages the arch wire 178 such as the place an active force against the arch wire, retaining the arch wire in the arch wire slot 116. It will be appreciated that a similar configuration is applicable to the mesial arm 120, mesial finger 132 and mesial transition portion 134, although not depicted in FIG. 12. With reference to FIGS. 9 and 12, the distal finger 126 is located at the respective distal side 108 and the mesial finger 132 is located at the respective mesial side 110 of the bracket body 102 and the arch wire slot 116. Therefore, the active retaining forces applied respectively by the distal finger 126 and the mesial finger 132 on the arch wire 178 are placed upon the arch wire 178 at the distal side 108 and the mesial side 110 of the self-ligating bracket 100 such as to maximize the active retensive force applied by the spring clip.

In still further exemplary embodiments, the bracket body 102 is secured to a bonding pad 106 exemplarily as described above. In an embodiment, the bonding pad 106 further includes a center guide line 180. The center guide line 180 exemplarily extends in the gingival-occlusal direction along the mesial-distal center line of the self-ligating bracket 100. The center guide line 180 provides a visual cue or guide to an orthodontist in order to facilitate placement of the self-ligating bracket 100 on a tooth of the patient's dentition.

In an exemplary embodiment for illustrative purposes the spring clip, and similarly, the bracket body, may be dimensioned such as to promote the features as described above while achieving a small size and low lingual-labial profile. Minimizing overall bracket size can improve patient comfort while receiving orthodontic treatment.

In an embodiment, the spring clip has an overall width of 0.117 in., length of 0.087 in., and a height of 0.018 in. Although the spring clip itself is only 0.010 in. thick, the added height comes from the transition portion which lowers the spring clip fingers by 0.008 relative to the spring clip arm bodies. The S-curve of the transition portions may use opposed 0.025 in. radiused curves.

The spring clip arm bodies may be 0.0125 in. wide and external 0.053 in length, while the projections from the clip fingers are 0.029 in. wide to the peaks of the projections. In an embodiment, the projections angle away from the end of the clip at a 30° angle. The center arm may have a length of 0.067 in. and a width of 0.045 in. with the cut out having a radius of 0.014 in.

While the invention has been described with reference to a preferred embodiment, those skilled in the art will appreciate that certain substitutions, alterations and omissions may be made without departing from the spirit thereof. Accordingly, the foregoing description is meant to be exemplary only and should not be deemed limitative on the scope of the invention set forth with the following claims.

The invention claimed is:

1. A self-ligating bracket comprising:
a bracket body having a mesial side opposed from a distal side and a labial side opposed from a lingual side, the bracket body comprising an arch wire slot that extends across the bracket body from the mesial side to the distal side and extends lingually into the bracket body from the labial side; and
a spring clip comprising a distal arm comprising a distal arm body and a distal finger and a mesial arm comprising a mesial arm body and a mesial finger, wherein the distal finger and the mesial finger are located lingual of the distal arm body and the mesial arm body in a different plane from the distal arm body and the mesial arm body, the spring clip is slidably secured to the bracket body and movable between a closed position and an open position;
wherein in the closed position, the distal finger and the mesial finger are positioned at least partially within the arch wire slot to occlude the arch wire slot; and
wherein in the open position, the distal arm and the mesial arm are deformed to move the distal finger and the mesial finger labially and out of the arch wire slot.

2. The self-ligating bracket of claim 1, wherein the spring clip is slidably secured to the bracket body in the gingival-occlusal dimension, and wherein in the closed position the distal finger and the mesial finger extend out of the bracket body into the arch wire slot and in the open position the distal finger and the mesial finger are withdrawn into the bracket body.

3. The self-ligating bracket of claim 2, wherein the distal arm and the mesial arm are slidably received within respective channels in the bracket body.

4. The self-ligating bracket of claim 3, wherein the respective channels comprise a distal channel and a mesial channel, and wherein the distal arm is slidably received within the distal channel that extends into the bracket body from the distal side and the mesial arm is slidably received within the mesial channel that extends into the bracket body from the mesial side.

5. The self-ligating bracket of claim 3, wherein the channels extend in gingivally from an occlusal side of the bracket body to the arch wire slot.

6. The self-ligating bracket of claim 3, wherein the channels extend in a gingival-occlusal and mesial-distal plane through the bracket body to the arch wire slot.

7. The self-ligating bracket of claim 1, wherein the distal arm body and the mesial arm body are co-planar in a first plane and the distal finger and the mesial finger are co-planar in a second plane and the first plane is different from the second plane.

8. The self-ligating bracket of claim 7, wherein the first plane is parallel to the second plane.

9. The self-ligating bracket of claim 7, wherein the first plane intersects the second plane.

10. The self-ligating bracket of claim 1, wherein the distal arm and the mesial arm deform in a mesial-distal direction as the spring clip is moved between the open and closed positions.

11. The self-ligating bracket of claim 10, wherein the distal finger comprises a distal projection and the mesial finger comprises a mesial projection and the distal projection and the mesial projection engage respective portions of the bracket body to deform the distal arm and the mesial arm in the mesial-distal direction as the spring clip moves between the closed position and the open position.

12. The self-ligating bracket of claim 11, wherein the distal arm and the mesial arm are slidably received within respective channels of the bracket body and the bracket body further comprises stop projections that extend into the respective channels, wherein engagement between the distal projection and the mesial projection with the respective stop projections deforms the distal arm and the mesial arm in the mesial-distal direction as the spring clip moves between the open position and the closed position.

13. The self-ligating bracket of claim 10, wherein deformation of the distal arm and the mesial arm in the mesial-distal direction stores potential energy in the spring clip which is released to assist moving the spring clip into the open position.

14. The self-ligating bracket of claim 10, wherein deformation of the distal arm and the mesial arm in the mesial-distal direction and deformation of the distal arm and the mesial arm in the labial dimension to move the distal finger and the mesial finger labially stores potential energy in the spring clip which is released as the spring clip is moved from the open position to the closed position to assist moving the spring clip into the closed position.

15. The self-ligating bracket of claim 1, wherein when the spring clip is in the closed position, the distal finger and the mesial finger engage a wall of the arch wire slot.

16. The self-ligating bracket of claim 1, further comprising:
a distal transition portion between the distal arm body and the distal finger; and
a mesial transition portion between the mesial arm body and the mesial finger.

17. The self-ligating bracket of claim 16, wherein the bracket body comprises:
a mesial shoulder and a distal shoulder which at least partially define a side of an arch wire slot;
wherein when the spring clip is in the closed position, the distal transition portion resiliently engages the distal shoulder and the mesial transition portion resiliently engages the mesial shoulder to bias the spring clip in the closed position.

18. The self-ligating bracket of claim 1, wherein the spring clip further comprises a center arm.

19. The self-ligating bracket of claim 18, wherein the bracket body further comprises:
a central channel transverse to the arch wire slot; and
a curved shoulder located within the central channel;
wherein the center arm terminates in a curved tip that resiliently engages the shoulder when the spring clip is in the closed position.

20. The self-ligating bracket of claim 1, wherein the arch wire slot is configured to receive an arch wire, and the distal finger and the mesial finger are configured to engage an arch wire received in the arch wire slot.

21. The self-ligating bracket of claim 1, wherein the spring clip is slidable in a gingival-occlusal direction relative to the bracket body between the open position and the closed position, and sliding movement of the spring clip in the gingival-occlusal direction causes the distal arm and the mesial arm to engage the bracket body and resiliently deform the distal arm and the mesial arm in the labial-lingual direction and resiliently deform the distal arm and the mesial arm in the mesial-distal direction.

* * * * *